United States Patent
Schreiber (10) Patent No.: US 9,895,202 B2
(45) Date of Patent: Feb. 20, 2018

(54) AIRFLOW-CHANNELING SURGICAL LIGHT SYSTEM AND METHOD

(71) Applicant: Kevin Joseph Schreiber, Happy Valley, OR (US)

(72) Inventor: Kevin Joseph Schreiber, Happy Valley, OR (US)

(73) Assignee: SLD Technology, Inc., Portland, OR (US)

(*) Notice: Subject to any disclaimer, the term of this patent is extended or adjusted under 35 U.S.C. 154(b) by 31 days.

(21) Appl. No.: 14/877,762

(22) Filed: Oct. 7, 2015

(65) Prior Publication Data

US 2017/0003015 A1 Jan. 5, 2017

Related U.S. Application Data (63) Continuation-in-part of application No. 14/789,338, filed on Jul. 1, 2015.

(51) Int. Cl.
*A61B 90/40* (2016.01)
*B01D 46/00* (2006.01)
(Continued)

(52) U.S. Cl.
CPC ............ *A61B 90/40* (2016.02); *A61B 90/30* (2016.02); *A61L 2/14* (2013.01); *A61L 2/16* (2013.01); *A61L 9/015* (2013.01); *A61L 9/22* (2013.01); *B01D 46/0047* (2013.01); *B01D 46/10* (2013.01); *F21V 33/0088* (2013.01); *A61B 2090/401* (2016.02); *F21W 2131/205* (2013.01)

(58) Field of Classification Search
CPC . F21V 33/0096; F21V 33/0088; A61B 90/30; A61B 90/40; A61B 2090/401; A61L 2/14; A61L 2/16; A61L 9/015; A61L 9/22; B01D 46/0047; B01D 46/10; F24F 3/056; F24F 13/078; F21W 2131/205
See application file for complete search history.

(56) References Cited

U.S. PATENT DOCUMENTS 2,449,362 A 9/1948 Bell
2,962,582 A 11/1960 Croft
(Continued)

FOREIGN PATENT DOCUMENTS

DE 3331299 A1 3/1985
EP 2679213 A2 1/2014
(Continued)

OTHER PUBLICATIONS

Oct. 31, 2016 Office Action issued in U.S. Appl. No. 14/789,338.
(Continued)

*Primary Examiner* — Bao Q Truong
(74) *Attorney, Agent, or Firm* — Barta, Jones & Foley, P.C.

(57) ABSTRACT

A light system includes a main body defining an internal chamber, a lighting assembly secured to the main body, and an airflow circuit extending around a periphery of the lighting assembly. The lighting assembly includes at least one light unit configured to emit light. The airflow circuit is configured to direct airflow out of the main body underneath the lighting assembly. The lighting assembly also includes an air cleansing device that is configured to cleanse the air passing through the airflow circuit.

8 Claims, 7 Drawing Sheets

(51) Int. Cl.
*B01D 46/10* (2006.01)
*A61L 9/22* (2006.01)
*A61L 9/015* (2006.01)
*A61L 2/14* (2006.01)
*A61L 2/16* (2006.01)
*A61B 90/30* (2016.01)
*F21V 33/00* (2006.01)
*F21W 131/205* (2006.01)

(56) References Cited

U.S. PATENT DOCUMENTS

| | | | |
|---|---|---|---|
| 3,792,230 A | 2/1974 | Ray | |
| 3,864,547 A | 2/1975 | Ray | |
| 4,356,535 A | 10/1982 | Chu | |
| 4,630,182 A | 12/1986 | Moroi et al. | |
| 5,443,625 A * | 8/1995 | Schaffhausen | B01D 46/0005 55/385.1 |
| 6,244,720 B1 | 6/2001 | Neff | |
| 7,083,659 B1 * | 8/2006 | Joyce | F21V 33/0088 55/385.1 |
| 7,144,140 B2 | 12/2006 | Sun et al. | |
| 7,682,054 B2 | 3/2010 | Hsu et al. | |
| 8,226,273 B2 | 7/2012 | Lai | |
| 8,319,408 B1 | 11/2012 | Horng | |
| 9,649,397 B2 * | 5/2017 | Ghilardi | A61L 2/07 |
| 9,707,310 B2 * | 7/2017 | Watanabe | A61L 9/205 |
| 2008/0305015 A1 * | 12/2008 | Ryu | A61L 9/22 422/122 |
| 2010/0196214 A1 * | 8/2010 | Graff | A61L 9/20 422/121 |
| 2013/0344795 A1 * | 12/2013 | Schreiber | F24F 13/078 454/293 |
| 2014/0185305 A1 * | 7/2014 | Takahashi | F21V 29/02 362/373 |
| 2014/0273803 A1 * | 9/2014 | Fontanesi | F21V 33/0088 454/293 |
| 2014/0293622 A1 | 10/2014 | Hauschulte | |

FOREIGN PATENT DOCUMENTS

| | | |
|---|---|---|
| FR | 2032919 A5 | 11/1970 |
| GB | 864894 A | 4/1961 |

OTHER PUBLICATIONS

Oct. 27, 2016 Search Report issued in International Patent Application PCT/US2016/040706.

Oct. 27, 2016 Written Opinion of the International Searching Authority issued in International Patent Application PCT/US2016/040706.

* cited by examiner

AIRFLOW-CHANNELING SURGICAL LIGHT SYSTEM AND METHOD

CROSS-REFERENCE TO RELATED APPLICATIONS

This is a Continuation-in-Part of application Ser. No. 14/789,338 filed Jul. 1, 2015. The disclosure of the prior application is hereby incorporated by reference herein in its entirety.

FIELD OF THE DISCLOSURE

Embodiments of the present disclosure generally relate to an airflow-channeling light system and method, such as may be used within a surgical operating room.

BACKGROUND OF THE DISCLOSURE

Hospital operating rooms typically include a surgical light that is positioned over a surgical site. The surgical light contains one or more light sources that are configured to emit a focused beam of light directly onto a surgical target zone.

Additionally, a supply air array is positioned within a ceiling directly above the surgical light and the surgical site target zone. The supply air array includes vents through which filtered air is supplied and directed toward the surgical site. The vents may include filters to filter the air that passes therethrough. Sidewall vents return contaminated air from the perimeter of the room to an air filtration system positioned upstream of the supply air array. The air filtration system supplies filtered air to the room through the supply air array with unidirectional, downward airflow.

Because the surgical light may be positioned directly over the surgical target zone, the surgical light may block airflow generated by the supply air array and create a low pressure zone underneath the surgical light. The low pressure zone causes air turbulence underneath the surgical light. Due to turbulent airflow, various contaminants generated through a surgical procedure may be circulated within the surgical environment. For example, surgical staff may carry particulate and bacterial contaminants that may be dispersed directly above a surgical site in the absence of filtered, downward, unidirectional flow. Further, bone fragments, biological fluids, and blood may be projected upward toward the surgical light head, which is cleaned and sterilized between surgical procedures.

Accordingly, a need exists for a system and method of providing uninterrupted, reduced turbulence airflow underneath a surgical light. A need exists for a system and method that reduce the possibility of contaminants being dispersed over and within a surgical site.

SUMMARY OF THE DISCLOSURE

Certain embodiments of the present disclosure provide a light system that includes a main body defining an internal chamber, a lighting assembly secured to the main body, and an airflow circuit extending around a periphery of the lighting assembly. The lighting assembly may include at least one light unit configured to emit light. The airflow circuit is configured to direct airflow out of the main body underneath the lighting assembly. The lighting assembly also includes an air cleansing device that is configured to cleanse the air passing through the airflow circuit.

The airflow circuit may be configured to direct the airflow out of the main body at an angle toward a central imaginary axis extending through and out of the lighting assembly. The airflow circuit may include an airflow outlet having an opening formed through an angled wall.

The light system may also include a protective insert coupled to the main body. The protective insert may include a support frame coupled to an airflow outlet of the airflow circuit. The support frame may include an internal airflow path that connects to one or more airflow passages. In at least one embodiment, the protective insert is removably secured to the main body, such as through a snap-fit, latching, press-fit, interference-fit, or other such connection. The internal airflow path may define at least a portion of a circuitous path that includes at least one turn that re-directs or otherwise shunts the airflow therein.

In at least one embodiment, the protective insert may include a transparent shield coupled to the support frame. The lighting assembly is configured to shine light through the transparent shield. The transparent shield may include a plurality of air passages formed therethrough. The light system is configured to direct airflow around the lighting assembly and out through the plurality of air passages.

The light system may also include a fan disposed within the internal chamber. The fan is configured to draw air into and through the airflow circuit.

The light system may also include a covering cap coupled to the main body. An air inlet passage may be defined between the covering cap and the main body.

The light system may also include an air filter disposed within the internal chamber. The air filter is configured to filter air passing through the airflow circuit.

Certain embodiments of the present disclosure provide an operating room that may include a floor connected to walls, and a ceiling connected to the walls. A surgical site is disposed at an area between the floor, the walls, and the ceiling. A supply air array may be coupled to the ceiling. The supply air array may include a plurality of air diffusers that are configured to direct air into the operating room. A surgical light system may be suspended from the ceiling by a support beam and at least one boom arm. The surgical light system may include a main body defining an internal chamber, a lighting assembly secured to the main body, and an airflow circuit extending around a periphery of the lighting assembly. The lighting assembly may include at least one light unit configured to emit light. The airflow circuit is configured to direct airflow out of the main body underneath the lighting assembly.

DETAILED DESCRIPTION OF THE DISCLOSURE

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Certain embodiments of the present disclosure provide an airflow-channeling surgical light system that may include an airflow circuit having one or more air paths that are configured to channel filtered air to a periphery or outer perimeter of a lighting assembly. The system is configured to deliver air directly under the lighting assembly. In at least one embodiment, the system may include a quick connect perimeter protective insert that includes a plurality of air passages. The positioning of the air passages prevents contaminants from easily entering the air path(s) and allows the perimeter protective insert to easily be removed for cleaning. The perimeter protective insert may also include a protective shield to lend additional support to the insert and also to help protect a light lens of the lighting assembly from contamination.

Figure 1:
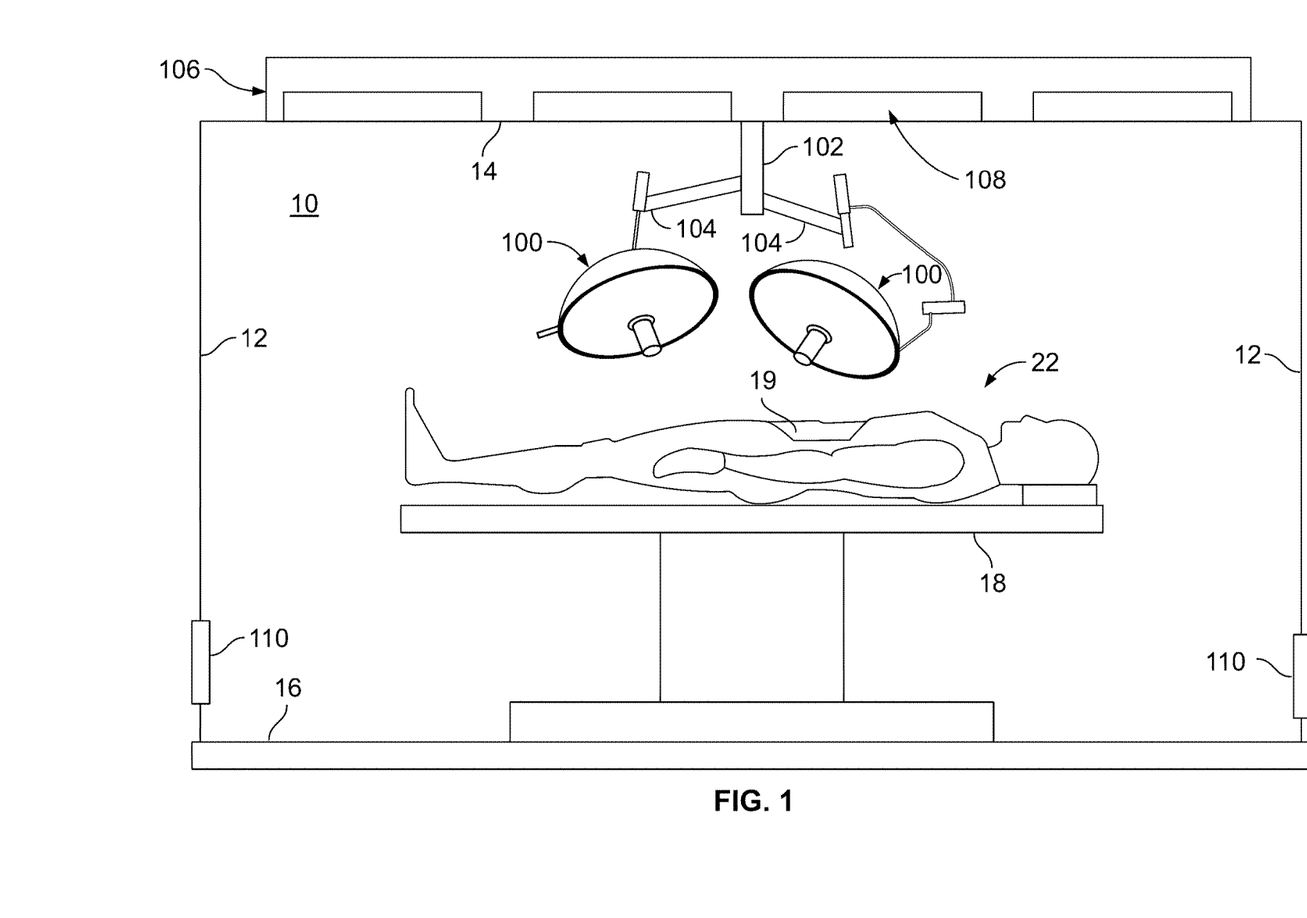
FIG. 1 illustrates a lateral view of an operating room, according to an embodiment of the present disclosure.

FIG. 1 illustrates a lateral view of an operating room 10, according to an embodiment of the present disclosure. The operating room 10 may be defined by walls 12, a ceiling 14, and a floor 16. An operating table 18 may be supported on the floor 16. The operating table 18 may include a support bed 20 that is configured to support a patient 22. A surgical site 19 may be located on the patient 22.

An airflow-channeling surgical light system 100 is suspended from the ceiling 14 above the operating table 18, which may define a sterile field. A support beam 102 extends downwardly from the ceiling 14. One or more boom arms 104 may extend from the support beam 102. The airflow-channeling surgical light system 100 connects to a boom arm 104. As shown in FIG. 1, two surgical light assemblies 100 may be coupled to two separate and distinct boom arms 104. Alternatively, more or less surgical light assemblies 100 than shown may be used.

A supply air array 106 may be secured above the ceiling 104, such as within a plenum. The supply air array 106 is configured to direct airflow into the operating room 10. The supply air array 106 may include one or more air diffusers 108 that are connected to one or more return vents 110, which may be secured to one or more walls 12. For example, the supply air array 106 directs airflow into the operating room through the diffusers 108. The airflow passes into the return vents 110, which channel the airflow back into the supply air array 106, where the airflow is filtered and directed back into the operating room through the air diffusers 108.

Figure 2:
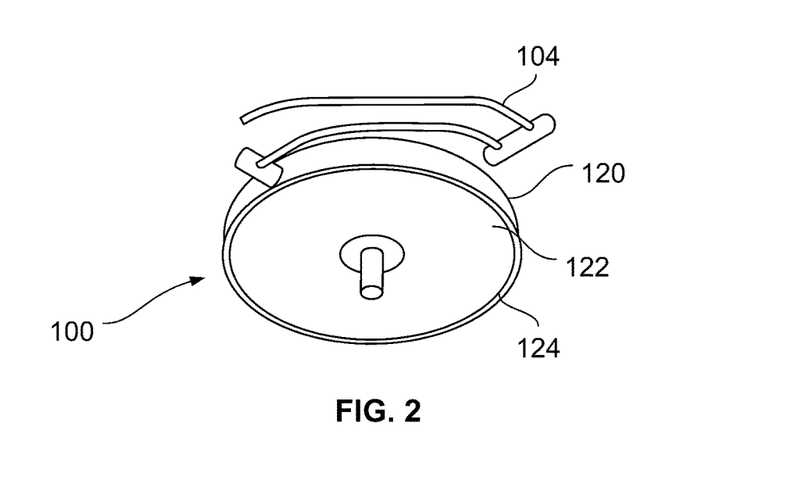
FIG. 2 illustrates a perspective bottom view of an airflow-channeling surgical light system, according to an embodiment of the present disclosure.

FIG. 2 illustrates a perspective bottom view of the airflow-channeling surgical light system 100, according to an embodiment of the present disclosure. The surgical light system 100 may include a main body 120 that is configured to couple to the boom arm 104. A lighting assembly 122 is secured to the main body 120 and may include one or more light units that are configured to direct light through the sterile field onto the surgical site 19. For example, the light units may be or include a plurality of light emitting diodes (LEDs). Optionally, the light units may be incandescent light bulbs, fluorescent light bulbs, halogen light bulbs, and/or the like.

An airflow outlet 124 is formed around the periphery of the lighting assembly 122. The periphery is the outer perimeter portion of the lighting assembly 122. An airflow circuit, including the airflow outlet 124, may also extend around other portions of the lighting assembly 122, such as top and bottom portions of the lighting assembly 122, as described below. The airflow outlet 124 is configured to direct airflow underneath the lighting assembly 122. The airflow outlet 124 does not extend through the lighting assembly 122. In at least one embodiment, an entire airflow circuit, which may include the airflow outlet 124, does not extend into or through the lighting assembly 122. Instead, the airflow circuit and outlet 124 extend around an outer perimeter or periphery of the lighting assembly 122. That is, the airflow circuit is routed around the lighting assembly 122 so as not to interfere with operation of the lighting assembly 122. A protective insert may be configured to be removably secured to the main body, such as to the airflow outlet 124.

Figure 3:
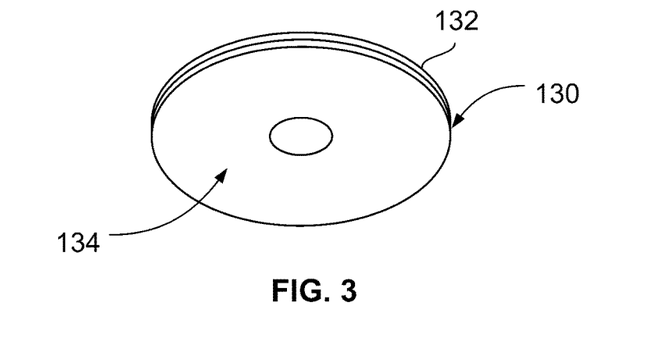
FIG. 3 illustrates a perspective bottom view of a protective insert, according to an embodiment of the present disclosure.

FIG. 3 illustrates a perspective bottom view of a protective insert 130, according to an embodiment of the present disclosure. The protective insert 130 may include a support frame 132 that is configured to be removably secured to and/or within the airflow outlet 124, such as within a retaining channel of a peripheral airflow channel. For example, the support frame 132 may be configured to snapably, latchably, or otherwise removably couple to the airflow outlet 124. In at least one embodiment, the support frame 132 may be configured to be secured within the airflow outlet 124 through an interference fit, a press fit, and/or the like.

The support frame 132 may include a plurality of air passages that are configured to receive airflow from the airflow outlet 124 and direct the airflow underneath the lighting assembly 122 (shown in FIG. 2). As shown, the support frame 132 may be shaped as a ring. Optionally, the support frame 132 may be formed as various other shapes and sizes, depending on the shape and size of the surgical light system 100.

The protective insert 130 may also include a transparent shield 134 that extends between interior edges of the support frame 132. The transparent shield 134 may be formed of glass, clear plastic, and/or the like. Optionally, the transparent shield 134 may be tinted. The transparent shield 134 is configured to extend beneath a lens and/or lower transparent surface of the lighting assembly 122. In this manner, the transparent shield 134 is configured to protect the lighting assembly 122 from contaminants. Alternatively, the protective insert 130 may not include the transparent shield 134.

In operation, the support frame 132 of the protective insert 130 is configured to provide a circuitous airflow path between the airflow outlet 124 and a volume beneath the surgical light system 100. As such, the support frame 132 reduces the possibility that contaminants (such as bacteria, bodily fluids, and the like) enter the airflow outlet 124. Further, the transparent shield 134 protects the lighting assembly 122 from contaminants. After a surgical operation, the protective insert 130 may be removed from the surgical light system 100 and cleaned in order to remove any contaminants thereon or therein.

Alternatively, the support frame 132 may be permanently fixed to the main body 120. For example, the support frame 132 may be permanently fixed to or otherwise within the airflow outlet 124.

Figure 4:
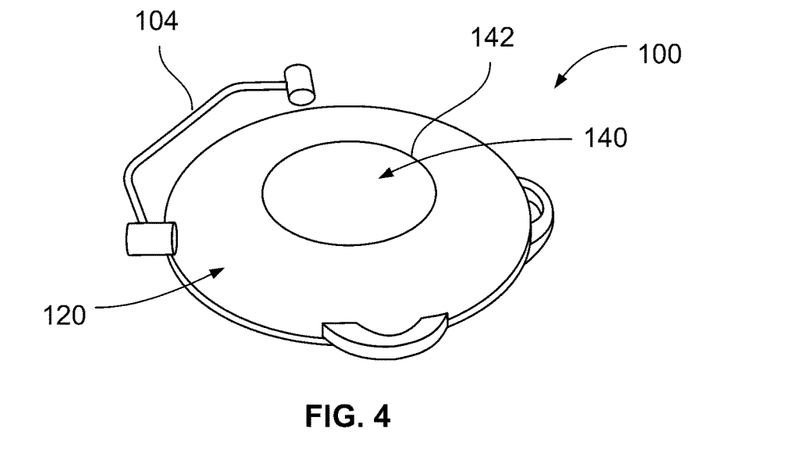
FIG. 4 illustrates a perspective top view of an airflow-channeling surgical light system, according to an embodiment of the present disclosure.

FIG. 4 illustrates a perspective top view of the airflow-channeling surgical light system 100, according to an embodiment of the present disclosure. A covering cap 140, such as a dome, may be secured over a portion of the main body 120. An air inlet passage 142 may be defined between a lower surface of the covering cap 140 and an upper surface of the main body 120. In operation, airflow is drawn into the main body 120 through the air inlet passage 142. The airflow is channeled from the air inlet passage 142 to an internal airflow circuit (such as formed by one or more conduits, pipes, passages, and/or the like), which channels the airflow around the lighting assembly 122 (shown in FIG. 2) and out of the system 100 by way of the airflow outlet 124 (shown in FIG. 2).

Figure 5:
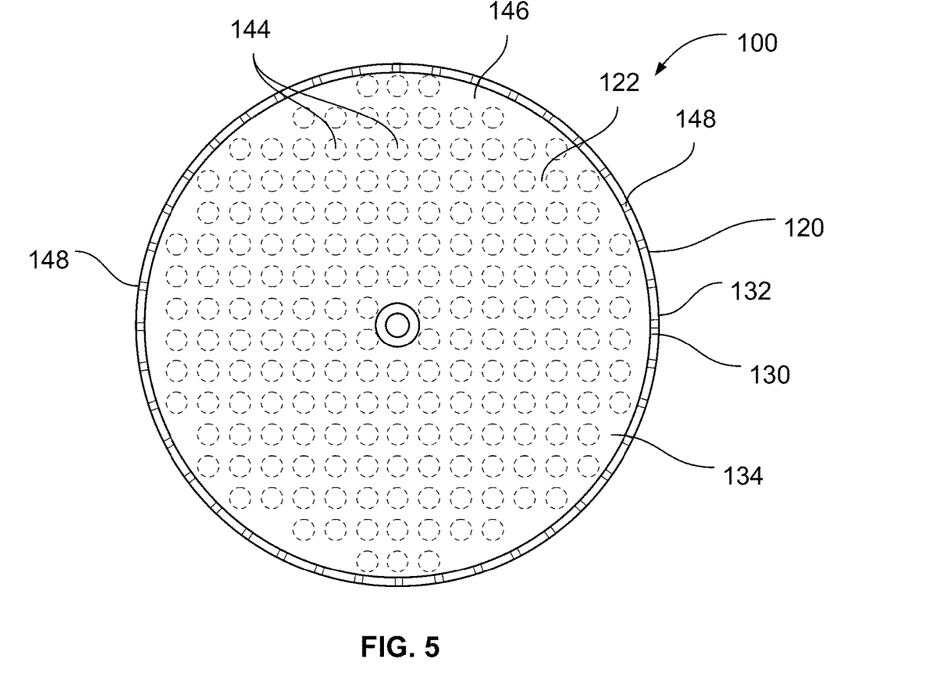
FIG. 5 illustrates a bottom view of an airflow-channeling surgical light system, according to an embodiment of the present disclosure.

FIG. 5 illustrates a bottom view of the airflow-channeling surgical light system 100, according to an embodiment of the present disclosure. The lighting assembly 122 may include a plurality of light units 144 above a lens or transparent panel 146. The transparent shield 134 of the protective ring 130 is disposed underneath the lens or transparent panel 146.

The support frame 132 of the protective insert 130 is secured within the airflow outlet 124. As noted, the airflow outlet 124 extends around a periphery of the lighting assembly 122. The support frame 132 may include a plurality of air outlet passages 148. The air outlet passages 148 may be disposed at a common level. Optionally, one or more air outlet passages 148 may be disposed at different levels than one or more other air outlet passages 148.

Figure 6:
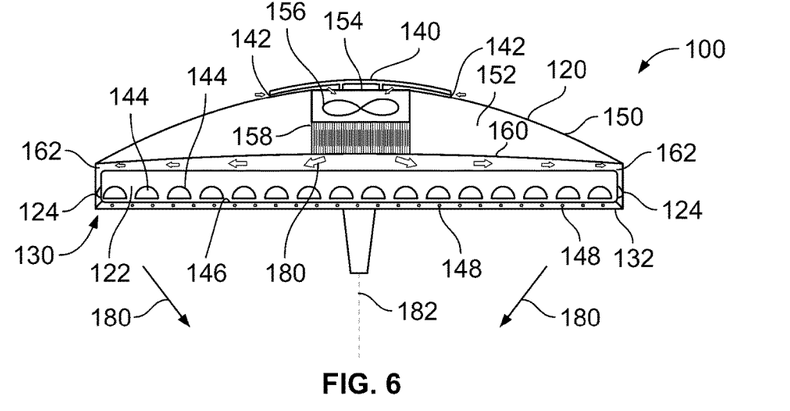
FIG. 6 illustrates a lateral internal view of an airflow-channeling surgical light system, according to an embodiment of the present disclosure.

FIG. 6 illustrates a lateral internal view of the airflow-channeling surgical light system 100, according to an embodiment of the present disclosure. The main body 120 may include an outer shroud 150 that defines an internal chamber 152. An opening 154 is formed through a top of the outer shroud 150. The covering cap 140 is secured to the main body 120 within the opening 154 such that the air inlet passage 142 forms (or otherwise is) a gap between a lower surface of the covering cap 140 and an upper surface of the outer shroud 150.

A fan 156 (such as an electric, piezoelectric, or other such fan) is secured within the internal chamber 152 underneath the covering cap 140. An air filter 158, such as a high-efficiency particulate arrestance (HEPA) filter, may be positioned underneath the fan 156. However, any air filtering device may be used, for example, any type of air filtering device that captures and/or contains contaminants, such as any device used to filter, trap or capture bacteria, viruses, mold, fungi, allergens, volatile organic compounds (VOCs), etc. Thus, in some embodiments, instead of a HEPA filter, an ultra low penetration air (ULPA) filter or an electrostatic filter may be used, among others.

An upper air channel 160 is secured above the lighting assembly 122. The upper air channel 160 may not extend into the lighting assembly 122. Instead, the upper air channel 160 provides an air conduit that extends over the lighting assembly 122. The upper air channel 160 connects to one or more lateral or peripheral air channels 162 that extend around a periphery of the lighting assembly 122. The airflow outlet 124 connects to the peripheral air channel 162. For example, the airflow outlet 124 may form a terminal end of the peripheral air channel 162. The airflow outlet 124 connects to the support frame 132 of the protective insert 130. Accordingly, an airflow circuit extends from the air inlet passage 142 through the fan 156 and the air filter 158. The airflow circuit continues from the fan 156 and the air filter 158 into the upper air channel 160, which connects to the peripheral air channel 162, and into the airflow outlet 124, which connects to the support frame 132, which includes the air outlet passages 148. Accordingly, the airflow circuit extends around the lighting assembly 122, and may not extend into the lighting assembly 122.

The upper air channel 160 may be one or more linear channels formed above the lighting assembly 122. Optionally, the upper air channel 160 may be an internal cavity that forms a disc shape within the main body 120. The peripheral air channels 162 may include one or more channels connecting to the upper air channel 160. For example, a single circumferential air channel 162 may circumferentially extend from the upper air channel 160.

As shown, flowing air (that is, airflow) enters the surgical light system 100 through the air inlet passage 142 and is directed out through the air outlet passages 148. The fan 156 is downstream from the air inlet passage 142. The air filter 158 is downstream from the fan 156. The upper air channel 160 is downstream from the air filter 158. The peripheral air channel 162 is downstream from the upper air channel 160. The airflow outlet 124 is downstream from the peripheral air channel 162 (or otherwise forms a downstream terminal portion of the peripheral air channel 162). The air outlet passages 148 of the protective insert 130 are downstream from the airflow outlet 124.

In operation, as the fan 156 is activated, the rotation of fan 156 draws in air outside of the surgical light system 100 through the air inlet passage 142. The fan 156 moves the air through the air filter 158, which filters contaminants from the air. The fan 156 continues to move the air through the air filter 158 and into the upper air channel 160. The air 180 is then channeled to the peripheral air channel 162 and out through the airflow outlet 124. The air 180 then passes through a circuitous air path within the support frame 132 and out through the air outlet passages 148. The air outlet passages 148 may be angled to shunt and direct the air 180 out of the system 100 at an angle towards a central imaginary axis 182 extending downwardly from a center of the lighting assembly 122. The axis 182 is "imaginary" in that it is a virtual axis that extends through and out of the lighting assembly 122.

The circuitous air path includes one or more turns that re-direct the airflow therein. For example, the turn(s) may cause the airflow to turn at a right angle. As another example, the turn(s) may cause the airflow to turn in an opposite direction from a previous direction of travel (for example, in a direction that is 180 degrees from the initial direction of travel).

Figure 7:
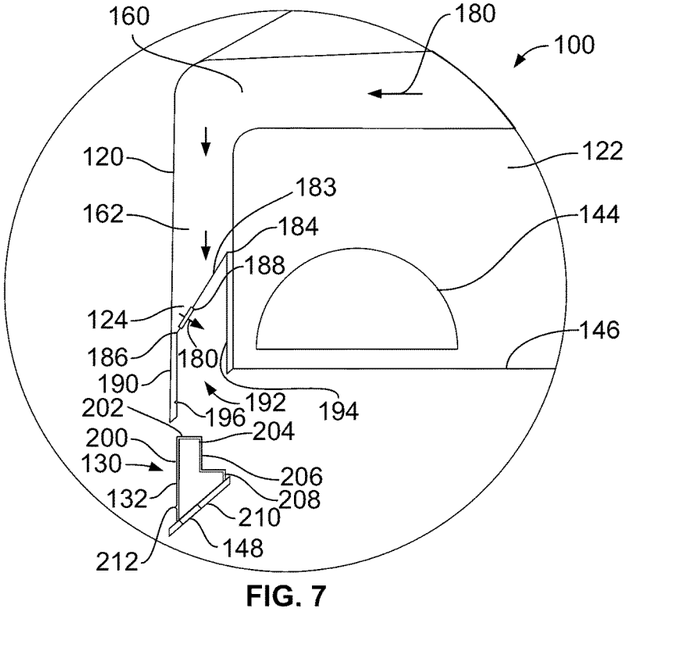
FIG. 7 illustrates a cross-sectional view of a support frame of a protective insert removed from an airflow outlet of an airflow-channeling lighting system, according to an embodiment of the present disclosure.

FIG. 7 illustrates a cross-sectional view of the support frame 132 of the protective insert 130 removed from the airflow outlet 124 of the airflow-channeling lighting system 100, according to an embodiment of the present disclosure. As shown, the airflow outlet 124 may be formed by an angled wall 183 that angles downwardly from an inboard area 184 (that is, closer to the central imaginary axis 182) to an outboard area 186 (that is, further from the central imaginary axis 182). An opening 188 is formed through the angled wall 183. The opening 188 allows air 180 to pass therethrough in a direction that is angled toward the central imaginary axis 182 (shown in FIG. 6).

The main body 120 may include a lower rim 190 that extends below the airflow outlet 124. A retaining channel 192 may be defined between an outer peripheral portion 194 of the lighting assembly 122 and the lower rim 190. The lower rim 190 may include a circumferential retaining divot 196.

The support frame 132 includes an outboard wall 200 that connects to an upper rim 202, which, in turn, connects to an inboard wall 204 having an opening 206 formed therethrough. The inboard wall 204 may connect to a support wall 208 that connects to an angled wall 210 having the air outlet passages 148 formed therethrough. A detent 212 (such as a ridge, lip, or other such protuberance) extends radially outward from the outboard wall 200 and is configured to be securely retained within the retaining divot 196. In this manner, the support frame 132 may be removably secured to the main body 120. Alternatively, the lower rim 190 may include the detent, while the support frame 132 includes retaining divot.

Figure 8:
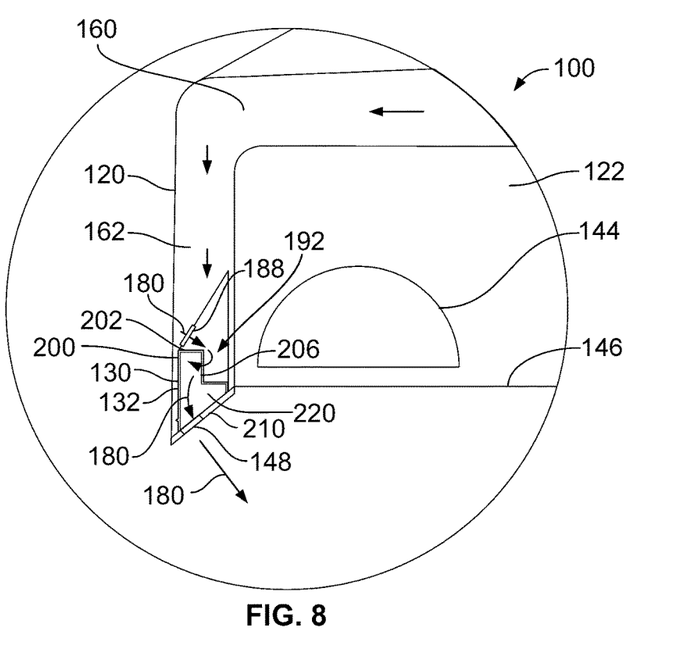
FIG. 8 illustrates a cross-sectional view of a support frame of a protective insert secured within a retaining channel that is in fluid communication with an airflow outlet of an airflow-channeling lighting system, according to an embodiment of the present disclosure.

FIG. 8 illustrates a cross-sectional view of the support frame 132 of the protective insert 130 secured within the retaining channel 192 that is in fluid communication with the airflow outlet 124 of the airflow-channeling lighting system 100, according to an embodiment of the present disclosure. The support frame 132 defines an internal air path 220 therein. The air path 220 extends from the opening 206 to the air outlet passages 148. As shown, air 180 passes out of the opening 180 of the airflow outlet 124 at an angle. The air 180 winds or otherwise turns around the upper rim 202 and enters air path 220 through the opening 206. The air 180 then passes out of the airflow outlet 180 through the air passages 148 at an angle defined by the angled surface of the angled wall 210. As shown, the air 180 is directed out of the support frame 132 at an angle toward the central imaginary axis 182 (shown in FIG. 6). As such, the airflow is directed underneath the lighting assembly 122.

A circuitous air path is formed between the airflow outlet 124 and the air outlet passages 148. The air 180 passes out of the air flow outlet 124 toward the central imaginary axis 182, but is shunted to double-back toward the outboard wall 200 of the support frame 132. The air 180 is then re-directed toward the central imaginary axis 182 by way of the air outlet passages 148 formed through the angled wall 210. The circuitous air path reduces the possibility that contaminants may pass into the peripheral channel 162, as there are structures (for example, the upper rim 202) that shield the opening 188 of the airflow passage 124 from being directly exposed to the surgical site 19 or any contaminants or debris within the sterile field or the room 10.

Referring to FIGS. 1-8, the surgical light system 100 forces air around a periphery of the lighting assembly 120 and out through the air outlet passages 148 of the protective insert 130. The forced air is directed underneath the lighting assembly 120. The delivery of the forced air underneath the lighting assembly 122 generates a pressure zone underneath the lighting assembly 122, which reduces air turbulence, thereby reducing the possibility of contaminants passing onto or into the surgical site 19 or back into the surgical light system 100.

The fan 156 and filter 158 may be interchangeably positioned within the internal chamber 152. The surgical light system 100 may be formed as various other shapes and sizes than shown. For shapes that are not round or symmetrical, a higher concentration of air openings 188 and/or air outlet passages 148 may be disposed along shorter lengths of the system 100 to balance the airflow with the longer sides.

Alternatively, the system 100 may not include the fan and/or the filter. Instead, the system 100 may be coupled to a separate, distinct, and remote air delivery source that is configured to move air through the airflow circuit.

As shown and described, the system 100 is configured to direct pressurized air underneath an entire lower surface of the lighting assembly 122 without blocking any light that is generated by the lighting assembly. Further, because the air is channeled around the lighting assembly (instead of through the lighting assembly), the density of light units within the lighting assembly may be maintained (instead of spreading light units apart to allow for air channels to be formed therebetween). The pressurized air underneath the lighting assembly 122 reduces turbulent recirculation of contaminants directly over the patient and surgical site. The protective insert 130 reduces the likelihood of blood, bone fragments, bodily fluids, or other contaminants from infiltrating into the airflow circuit. The protective ring 130 may be removed from the system 100 after a procedure to be cleaned.

Embodiments may be used in relation to a hospital operating room environment. Optionally, embodiments of the present disclosure may be used in various other settings in which pressurized airflow is to be directed underneath a lighting assembly. For example, embodiments of the present disclosure may be used in dental offices, manufacturing clean rooms, residential spaces, and the like.

Figure 9:
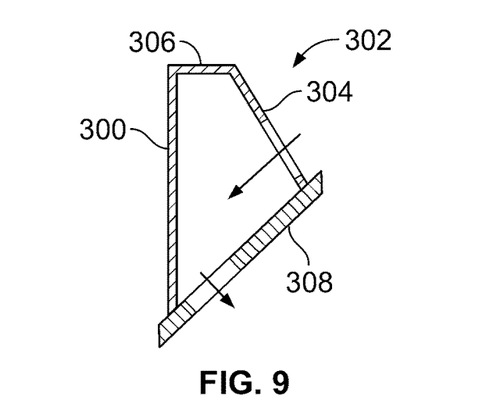
FIG. 9 illustrates a cross-sectional view of a support frame of a protective insert, according to an embodiment of the present disclosure.

FIG. 9 illustrates a cross-sectional view of a support frame 300 of a protective insert 302, according to an embodiment of the present disclosure. The support frame 300 is similar to the support frame 132, except that a single linear wall 304 extends from the upper rim 306 to the angled wall 308. The support frame 300 may be sized and shaped differently than shown. For example, a curved airflow path may be formed through therethrough. The support frame 300 may be used with any of the embodiments of the present disclosure.

Figure 10:
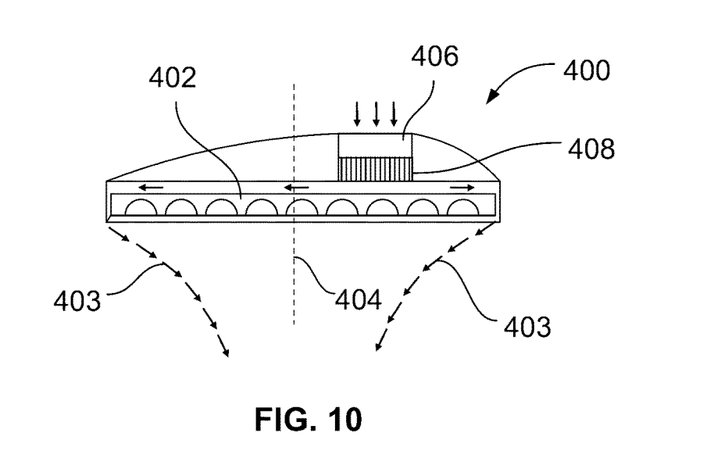
FIG. 10 illustrates a lateral internal view of an airflow-channeling surgical light system, according to an embodiment of the present disclosure.

FIG. 10 illustrates a lateral internal view of an airflow-channeling surgical light system 400, according to an embodiment of the present disclosure. The system 400 is similar to the system 100 and is configured to direct airflow 403 outwardly around a periphery of a lighting assembly 402 at an angle toward a central imaginary axis 404 of the system 400. The system 400 includes a fan 406 and an air filter 408 that may be offset from the central imaginary axis 404. The position of the fan 406 and the air filter 408 as shown in FIG. 10 may be used with respect to any of the embodiments of the present disclosure.

Figure 11:
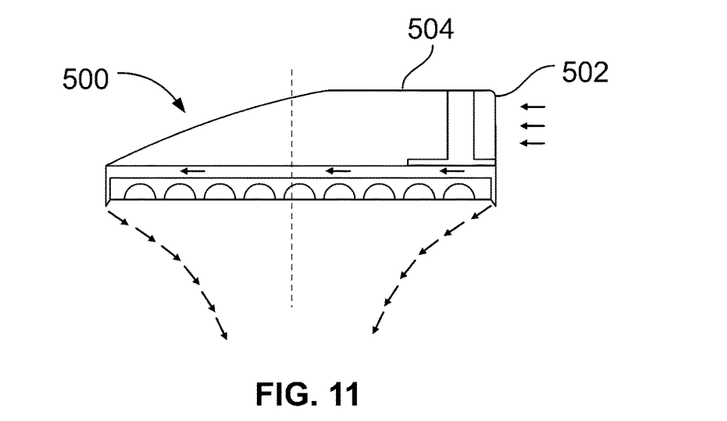
FIG. 11 illustrates a lateral internal view of an airflow-channeling surgical light system, according to an embodiment of the present disclosure.

FIG. 11 illustrates a lateral internal view of an airflow-channeling surgical light system 500, according to an embodiment of the present disclosure. In this embodiment, air inlet passages 502 may be formed through a side (instead of a top) of a main body 504. The air inlet passages 502 as shown in FIG. 11 may be used with respect to any of the embodiments of the present disclosure.

Figure 12:
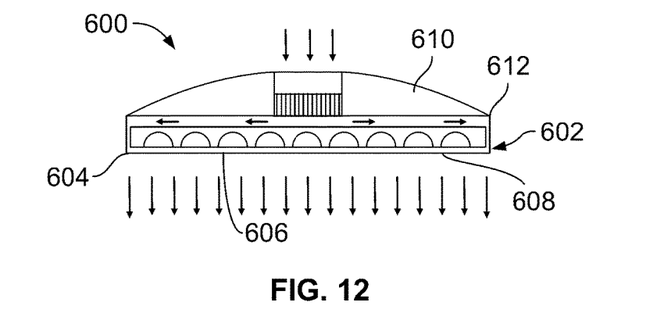
FIG. 12 illustrates a lateral internal view of an airflow-channeling surgical light system, according to an embodiment of the present disclosure.

FIG. 12 illustrates a lateral internal view of an airflow-channeling surgical light system 600, according to an embodiment of the present disclosure. The system 600 may include a protective insert 602 having a support frame 604 connected to a transparent shield 606. An air chamber 608 may be defined between a lens or transparent panel 610 of the lighting assembly 612 and the transparent shield 606. A plurality of air passages may be formed through the transparent shield 606. As such, air may be directed into the air chamber 608 and forced through the air passages underneath the lighting assembly 612.

Figure 13:
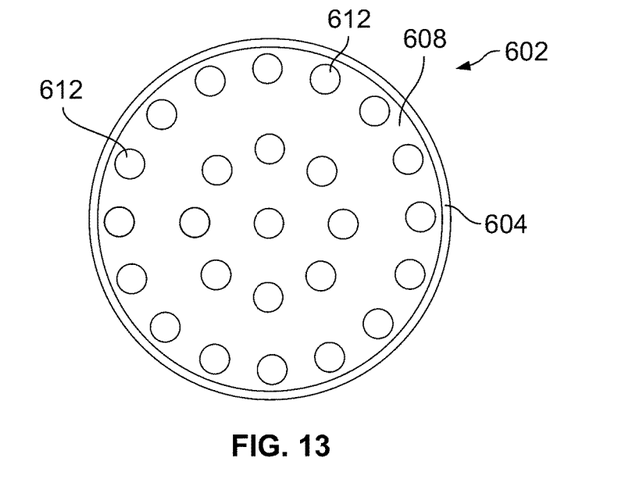
FIG. 13 illustrates a bottom view of a protective insert, according to an embodiment of the present disclosure.

FIG. 13 illustrates a bottom view of the protective insert 602, according to an embodiment of the present disclosure. As shown, a plurality of air passages 612 are formed through the transparent shield 606. The protective insert 602 shown and described with respect to FIGS. 12 and 13 may be used with any of the embodiments of the present disclosure.

Figure 14:
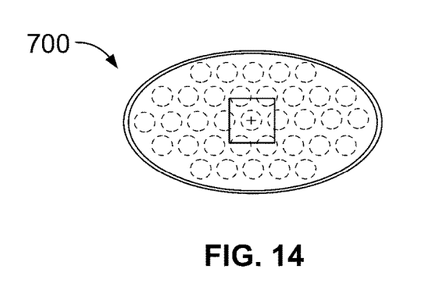
FIG. 14 illustrates a bottom view of an airflow-channeling surgical light system, according to an embodiment of the present disclosure.

FIG. 14 illustrates a bottom view of an airflow-channeling surgical light system 700, according to an embodiment of the present disclosure. As shown, the system 700 may be elliptical, instead of circular.

Figure 15:
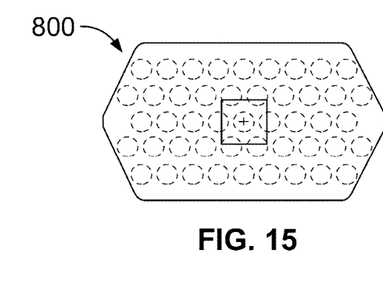
FIG. 15 illustrates a bottom view of an airflow-channeling surgical light system, according to an embodiment of the present disclosure.

FIG. 15 illustrates a bottom view of an airflow-channeling surgical light system 800, according to an embodiment of the present disclosure. As shown, the system 800 may include linear outer edges. In general, the light systems shown and described may be various shapes and sizes, such as square, rectangular, triangular, circular, elliptical, ovoid, irregularly-shaped, and/or the like. Additionally, the light systems may be configured with concentric rings with an air void between or around them.

Figure 16:
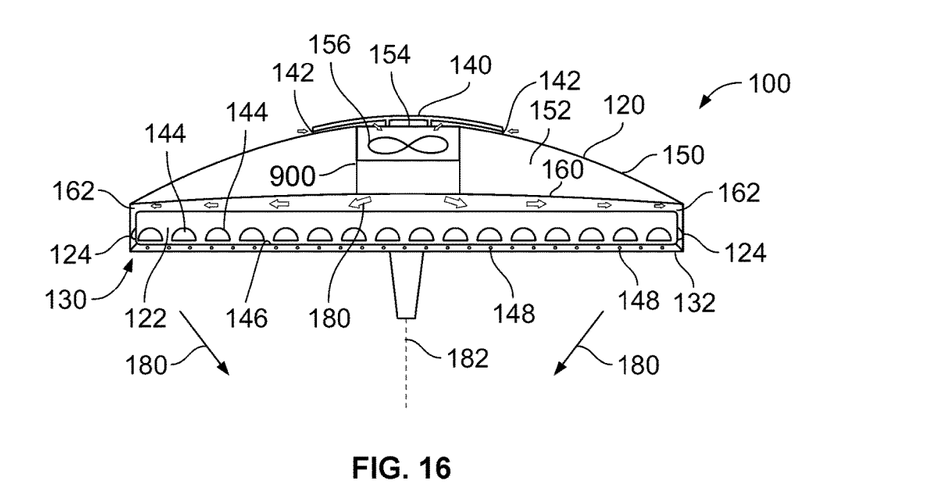
FIG. 16 illustrates a lateral internal view of an airflow-channeling surgical light system, according to another embodiment of the present disclosure.
Figure 17:
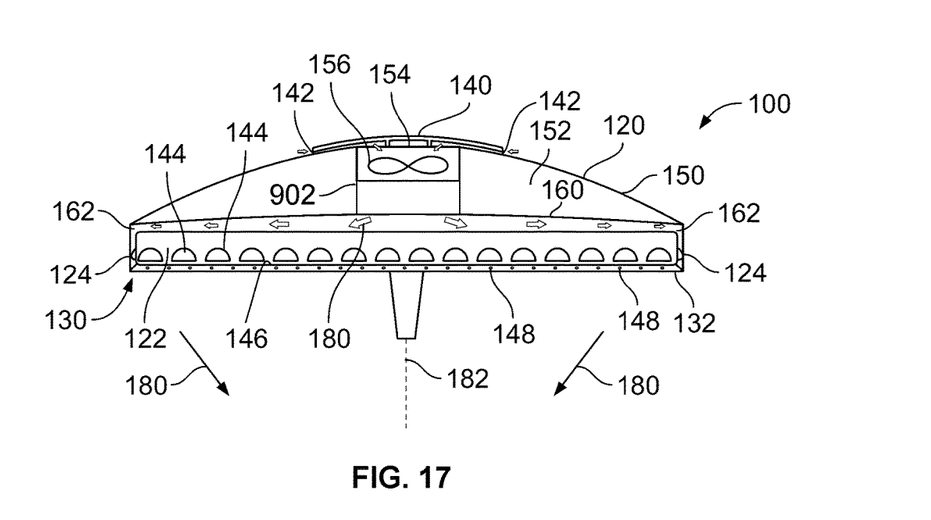
FIG. 17 illustrates a lateral internal view of an airflow-channeling surgical light system, according to another embodiment of the present disclosure.

Variations and modifications to the various embodiments are contemplated. For example, FIGS. 16 and 17 illustrate lateral internal views of the airflow-channeling surgical light system 100, according to others embodiments of the present disclosure. It should be noted that like numerals represent like parts in the various Figures. Similar to the embodiment illustrated in FIG. 6, in the embodiments illustrated in FIGS. 16 and 17, the main body 120 may include the outer shroud 150 that defines the internal chamber 152. The opening 154 is formed through the top of the outer shroud 150. The covering cap 140 is secured to the main body 120 within the opening 154 such that the air inlet passage 142 forms (or otherwise is) a gap between the lower surface of the covering cap 140 and the upper surface of the outer shroud 150.

The fan 156 (such as an electric, piezoelectric, or other such fan) is secured within the internal chamber 152 underneath the covering cap 140. Unlike the embodiment illustrated in FIG. 6, the embodiments illustrated in FIGS. 16 and 17 do not include the air filter 158 (e.g., a particulate arrestor), but instead include different air cleansing devices configured to sterilize or purify the air flow. However, it should be appreciated that although FIGS. 16 and 17 illustrate types of sterilizing and purifying devices, different types of sterilizing or purifying devices may be used. Additionally, different types of air filtering devices may be used instead of the illustrated air filter 158. In one or more embodiments, a device is positioned underneath the fan 156 in the air flow path thereof to at least one of filter, sterilize or purify the air flow generated by the fan 156. For example, the air cleansing device may be any type of mechanical or electrical air filtering device, air sterilizing device and/or air purifying device that is in the air flow path of the fan 156, which may, for example, remove particulates from the air flow, cleanse the air and/or deliver cleaning agents or chemicals in the air flow, among providing other air filtering, air sterilizing or air purifying arrangements.

More particularly, in the embodiment illustrated in FIG. 16, the air cleansing device is an air sterilizing device 900 that may be positioned underneath (or above) the fan 156 or may be in communication remotely to the surgical light system 100. The air sterilizing device 900 may be any type of device that effects a sterilization of the air flow from the fan 156, which may include introducing or adding a cleansing or sterilizing agent or chemical into the air flow path from the fan 156. Thus, the air sterilizing device 900 in various embodiments removes or changes the material properties of the contaminants or air particles to sterilize the air flow that is thereafter delivered as discussed herein. For example, the air sterilizing device 900 device may inject a cleansing or sterilizing agent or chemical into the air flow path that not only sterilizes or sanitizes the air, but also sterilizes or sanitizes the surfaces through which the air flows. It should be noted that any type of sterilizing or sanitizing method may be performed by the air sterilizing device 900, which in some embodiments may include using non-chemical methods to perform the sterilizing or sanitizing.

In the embodiment illustrated in FIG. 17, the air cleansing device is an air purifying device 902 that may be positioned underneath the fan 156. The air purifying device 902 may be any type of device that purifies the air flow from the fan 156. Thus, the air purifying device 902 in various embodiments changes the material properties of the contaminants or air particles to purify the air flow that is thereafter delivered as discussed herein. For example, the air purifying device 902 device may use one or more air ionization processes to purify the air flow, which can also effect a cleansing or purifying of the surfaces through which the air flows. It should be noted that any type of purifying method may be performed by the air purifying device 902, which in some embodiments may include using non-ionization methods to perform the sterilizing or sanitizing (e.g., different types of UV lights and catalysts).

It should be appreciated that any air purifying device may be used in or with one or more embodiments. For example, in one or more embodiments, any type of air purifying device that removes contaminants and sanitizes both the air and surfaces may be used. In some embodiments, the air purifying device 902 is any device used to kill, render impotent or reduce bacteria, viruses, mold, fungi, allergens, VOCs, etc. Some examples of the air purifying device 902 include, but are not limited to ultraviolet (UV) light, vaporized hydrogen peroxide (VHP), nano technology, ionization, bi-polar ionization, hydroxyl radicals, hydroperoxides, etc.

Additionally, it should also be appreciated that one or more air filtering, air sterilizing and/or air purifying devices or methods described herein may be used in combination with each other, for example, in a multi-stage cleaning design.

It should be noted that the other components of the airflow-channeling surgical light system 100 illustrated in FIGS. 16 and 17 are the same as the components described herein with respect to the airflow-channeling surgical light system 100 illustrated in FIG. 6 and will not be described again.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A light system comprising:
   a main body defining an internal chamber;
   a lighting assembly secured to the main body, wherein the lighting assembly comprises at least one light unit configured to emit light;
   an airflow circuit extending around a periphery of the lighting assembly, wherein the airflow circuit is configured to direct airflow out of the main body underneath the lighting assembly; and
   an air cleansing device, wherein the air cleansing device comprises an air sterilizing device that is configured to sterilize the air passing through the airflow circuit and to sterilize one or more surfaces of the airflow circuit.

2. The light system of claim 1, wherein the air sterilizing device is configured to introduce a cleansing or sterilizing agent or chemical into the air passing through the airflow circuit.

3. The light system of claim 2, wherein the cleansing or sterilizing agent or chemical comprises a substance that sterilizes or sanitizes the air and the one or more surfaces of the airflow circuit.

4. The light system of claim 1, wherein the air cleansing device comprises an air purifying device.

5. The light system of claim 4, wherein the air purifying device is configured to perform an air ionizing process on the air passing through the airflow circuit.

6. The light system of claim 1, wherein the air cleansing device comprises an air filtering device.

7. The light system of claim 6, wherein the air filtering device comprises a high-efficiency particulate arrestance (HEPA) filter.

8. The light system of claim 1, wherein the air sterilizing device is configured to inject a sterilizing chemical substance into the airflow circuit to sterilize the air passing through the airflow circuit and the one or more surfaces of the airflow circuit to remove or change one or more material properties of contaminants or air particles within the airflow circuit.

* * * * *